United States Patent
Edgett et al.

(10) Patent No.: US 10,342,756 B2
(45) Date of Patent: Jul. 9, 2019

(54) HYDRATING LIP BALM COMPOSITION

(71) Applicant: Carma Laboratories, Inc., Franklin, WI (US)

(72) Inventors: Keith Edgett, Hartland, WI (US); Louis DeFranco, Kenosha, WI (US)

(73) Assignee: Carma Laboratories, Inc., Franklin, WI (US)

( * ) Notice: Subject to any disclaimer, the term of this patent is extended or adjusted under 35 U.S.C. 154(b) by 0 days.

(21) Appl. No.: 15/621,421

(22) Filed: Jun. 13, 2017

(65) Prior Publication Data

US 2017/0354589 A1 Dec. 14, 2017

Related U.S. Application Data

(60) Provisional application No. 62/349,302, filed on Jun. 13, 2016.

(51) Int. Cl.
*A61Q 19/00* (2006.01)
*A61K 8/92* (2006.01)

(52) U.S. Cl.
CPC .............. *A61K 8/927* (2013.01); *A61K 8/922* (2013.01); *A61Q 19/001* (2013.01)

(58) Field of Classification Search
None
See application file for complete search history.

(56) References Cited

U.S. PATENT DOCUMENTS

| 2016/0310374 A1* | 10/2016 | Debeaud | A61K 8/31 |
| 2016/0324763 A1* | 11/2016 | Wu | A61Q 5/12 |
| 2017/0252288 A1* | 9/2017 | Lesniak | A61K 8/27 |
| 2018/0153793 A1* | 6/2018 | Constantine | A61K 8/732 |

OTHER PUBLICATIONS

Fleck, C. et al. Advanced Skin Care—A Novel Ingredient. J of the American College of Clinical Wound Specialists 4:92-94, 2012. (Year: 2012).*
International Search Report and Written Opinion for Application No. PCT/US2017/37194 dated Sep. 9, 2017 (11 pages).
Cupuacu Lip Balm. Publication (online). Humblebee & Me, Apr. 2013 (retrieved on Aug. 11, 2017). Retrieved from the internet: <URL: http://www.humblebeeandme.com/cupuacu-lip-balm/>; p. 3 lines 1-6.

* cited by examiner

*Primary Examiner* — Ralph J Gitomer
(74) *Attorney, Agent, or Firm* — Michael Best & Friedrich LLP

(57) ABSTRACT

The invention is directed to a composition comprising a first low-melt wax, a second low-melt wax, a high-melt wax, one or more oil phases, and optionally a flavoring agent.

24 Claims, No Drawings

HYDRATING LIP BALM COMPOSITION

CROSS-REFERENCE TO RELATED APPLICATIONS

This application claims the benefit of U.S. Provisional Application No. 62/349,302, filed Jun. 13, 2016, which is incorporated by reference herein.

BACKGROUND

Although lip balms are commercially available to soothe chapped lips, some of these compositions have a base which includes a combination of a wax and a mineral oil, or a combination of a wax and a petroleum jelly. The mineral oil or the petroleum jelly allows the lip balm to be transferred or applied to the lips, while the wax holds the composition on the lips, sealing the surface and allowing for the skin to build up its natural moisture level by minimizing moisture loss on the surface. However the correct ratios for the wax and petroleum jelly, or wax and mineral oil, are difficult or nearly impossible to obtain. The resulting product is either too stiff (due to the wax) or too greasy (due to the petroleum jelly or the mineral oil). Thus, there is a need for an improved lip balm composition.

SUMMARY

In an aspect, the invention provides a composition comprising: a first low-melt wax; a second low-melt wax; a high-melt wax; one or more oil phases; and optionally a flavoring agent.

In another aspect, the invention provides a method of sooth of moisturizing, soothing, or healing of external tissues comprising applying an effective amount of the composition to the tissue.

In yet another aspect, the invention provides a method of moisturizing or alleviating dry, chapped, or irritated lips comprising applying an effective amount of the composition to the lips.

DETAILED DESCRIPTION

The present invention provides a composition comprising low-melt waxes. Suitably, the composition may be used to alleviate dry, chapped, or irritated skin. More suitably, the composition may be a lip balm. The composition of traditional lip balms deposit a waxy or greasy residue on the skin to prevent moisture release. By using low-melt waxes, the present invention is able to provide non-waxy and non-greasy protection to external tissues, while delivering significant emolliency and improved moisture to remediate dry, chapped, or irritated skin. The composition uses body temperature to change the phase of the product upon application to facilitate spreading and absorption. The formulations comprise very unique sensory properties while delivering acceptable stability during transit, in storage, and during use.

Before any embodiments of the invention are explained in detail, it is to be understood that the invention is not limited in its application to the details of construction and the arrangement of components set forth in the following description. The invention is capable of other embodiments and of being practiced or of being carried out in various ways.

1. Definitions

Unless otherwise defined, all technical and scientific terms used herein have the same meaning as commonly understood by one of ordinary skill in the art. In case of conflict, the present document, including definitions, will control. Suitable methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an," and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "low-melt," as used herein, refers to a composition with a melting temperature between about 20° C. to about 50° C. The term "high-melt," as used herein, refers to a composition with a melting temperature greater than about 50° C.

As used herein, "butter" (also "botanical butter") is a triglyceride comprising saturated and unsaturated fatty acids. A butter may be further defined as a fat and/or oil extract of a plant fruit and/or seed characterized by having emollient properties and a low melting point ("low-melt") near human body temperature. Butter has the meaning as defined and is distinguished from a conventional high-melt wax and/or a non-jojoba ester. A butter includes both pure extracts from a plant fruit or seed and/or extract from a plant fruit or seed combined with additional lipid material to achieve the melting point characteristic and/or lubricity. Suitably, the lipid material is derived from a botanical source.

2. Composition

In one aspect, the invention provides a composition comprising a first low-melt wax, a second low-melt wax, a high-melt wax, an oil phase, and optionally a flavor. Suitably, the first low-melt wax may be present in an amount of about 15.0% to about 45.0% by weight, and the second low-melt wax may be present in an amount of about 15.0% to about 45.0% by weight. More suitably, the first low-melt wax may be present in an amount of about 28.0% to about 38.0% by weight, and the second low-melt wax may be present in an amount of about 25.0% to about 35.0% by weight. In embodiments, the first low-melt wax may comprise Cupuaçu butter, and the second low-melt wax may comprise *Murumuru* butter.

In embodiments, the first and/or second low-melt wax may be refined, and/or contain tocopherol and peptides. Suitably, the total mixed concentration of the first low-melt wax and the second low-melt wax may be present in an amount of about 30% to about 80% by weight. In a more suitable embodiment, the total mixed concentration of the first low-melt wax and/or the second low-melt wax may be present in an amount of about 40% to about 65% by weight. Suitably, the melting temperature of the first low-melt wax may be between about 25° C. and about 37° C., and/or the melting temperature of the second low-melt wax may be between about 25° C. and about 37° C.

Any suitable high-melt wax can be used in the inventive composition, many of which are known in the art and commercially available, such as, but not limited to, paraffin wax, beeswax, candellia wax, carnauba wax, and jojoba wax. In a suitable embodiment, the high-melt wax is beeswax. Suitably, the high-melt wax is present in an amount of about 18.6% to about 27.0%. The high-melt wax may be derived from any suitable source, such as but not limited to, a plant source or a synthetic source. In a suitable embodiment, the high-melt wax is beeswax. A suitable high-melt wax may have a melting temperature greater than 37° C. More suitably, the high-melt wax may have a melting temperature greater than 50° C. Other waxes may also be present in the composition.

In embodiments, the composition further comprises one or more oils. Exemplary oils suitable for use in the composition include, but are not limited to, sunflower oil, coconut oil, castor oil, vegetable oil, corn oil, canola oil, soybean oil, jojoba oil, olive oil, babassu oil, avocado oil, apricot oil, meadowfoam seed oil, macadamia seed oil, oat kernel oil, palm seed oil, safflower oil, sandalwood oil, sesame oil, sunflower oil, almond oil, wheat germ oil, cranberry seed oil, daikon seed oil, and combinations thereof. See International Patent Application EP2088995 A1. In embodiments, the composition may comprise more than one oil. In a suitable embodiment, the oil(s) may be present in an amount of about 1.0% to about 8.0% by weight of the composition. In a suitable embodiment, the oil may comprise sunflower oil. More preferably, the sunflower oil may be present in an amount of about 5.0% by weight. In another suitable embodiment, the oil may comprise cranberry seed oil and daikon seed oil. More suitably, the cranberry seed oil may be present in an amount of about 1.0%, and the daikon seed oil may be present in an amount of about 6.7%.

Suitably, the ratio of the first low-melt wax to the second low-melt wax is about 1:1 in the composition. More suitably, the ratio of the Cupuaçu butter to the *Murumuru* butter is about 1:1 in the composition. In embodiments, the ratio of the combined first and second low-melt waxes to the high-melt wax is about 1:1 to about 2:1. More suitably, the ratio of the Cupuaçu butter and the *Murumuru* butter to the high-melt wax is about 1:1 to about 2:1. In embodiments, the ratio of the combined first and second low-melt waxes to the oil phase is about 2.5:1 to about 11:1. More suitably, the ratio of the combined Cupuaçu butter and *Murumuru* butter to the oil phase is about 2.5:1 to about 11:1.

In embodiments, the composition of this invention may optionally include a flavoring agent to provide a sweet and pleasant taste, such as a sugar, which is of particular benefit if the composition is to be used orally. Fragrances and aromas that enhance different senses may also be added to the compositions of this invention. The desired fragrance may be obtained by including an essential oil, such as but not limited to, lavender, peppermint, tea tree oil, and eucalyptus. Colorants may be added to obtain a desirable colorimetric appearance. The colorant may be of an amount, particle size, and/or presented in a matrix that may permit transfer of colorant that imparts a color to an external tissue during application. The colorant may be a natural colorant such as for example, plant extracts, natural minerals, or carmine, or an artificial colorant.

The composition may optionally comprise one or more suitable additives, such as, but not limited to, a medicament (such as, for example, a sunscreen, an anti-oxidant, salicylic acid, and derivatives of salicylic acid), a soothing agent (such as, but not limited to, menthol, camphor, and eucalyptus), or a cosmetic. Other suitable additives include aloe vera gel, ascorbyl palmitate, and tocopherol.

In embodiments, the composition of the present invention is a solid at room temperature and melts when contacted with an external tissue at body temperature. The composition of the present invention may be formulated as a lip balm, lip butter, or a skin moisturizer (such as, but not limited to, a facial moisturizer or a body moisturizer).

In embodiments, the composition of the present invention may be marketed in any suitable container, such as for example, a tube or a small wide-mouth jar.

The invention further provides a method of soothing, moisturizing, or healing of external tissues comprising applying an effective amount of the composition described herein to the tissue. In embodiments, the tissue may be lip tissue. The present invention further provides a method of moisturizing or alleviating dry, chapped, or irritated lips comprising applying an effective amount of the composition described herein to the lips.

In embodiments, the invention exhibits improved stability compared to traditional lip balms, which can become extremely soft and melt in hot environments, such as in a car, a bag, or a pocket. Improved stability may be measured by, for example, needle penetration. Suitably, a lower needle penetration result indicates a more rigid composition. More suitably, the composition retains its form, shape, and/or structure under normal consumer-use conditions or in high temperatures, without melting, breaking, or falling out of the applicator. Even more suitably, upon the addition of energy to the composition, such as but not limited to, pressure and/or sheering, the composition may be transferred to the lip in a soft and soothing manner without depositing a heavy, waxy, residue, to provide long lasting moisture, relief, and a healthy appearance.

EXAMPLES

The following examples illustrate embodiments of the composition of the present invention.

Example 1

A composition was prepared with the constituents specified in Table 1:

TABLE 1

| Formulation A | |
|---|---|
| Ingredient | Weight % of composition |
| Cupuaçu butter | 30% |
| *Murmuru* butter | 28% |
| Beeswax | 27% |
| Sunflower oil | 5.0% |
| Flavor | 6.0% |

Example 2

A composition was prepared with the constituents specified in Table 2:

TABLE 2

| Formulation B | |
|---|---|
| Ingredient | Weight % of composition |
| Cupuaçu butter | 16% |
| *Murmuru* butter | 3.5% |
| Beeswax | 18.6% |
| Cranberry seed oil | 1.0% |
| Diakon seed oil | 6.7% |
| Flavor | 6.0% |

Example 3

A composition is prepared with the constituents specified in Table 3:

TABLE 3

| Formulation C | |
|---|---|
| Ingredient | Weight % of composition |
| Cupuaçu butter | 20% |
| *Murmuru* butter | 5% |
| Beeswax | 15% |
| Cranberry seed oil | 1% |
| Diakon seed oil | 19% |
| Flavor | 6% |

Example 4

A composition is prepared with the constituents specified in Table 4:

TABLE 4

| Formulation D | |
|---|---|
| Ingredient | Weight % of Composition |
| Cupuaçu butter | 25% |
| *Murmuru* butter | 10% |
| Beeswax | 10% |
| Castor seed oil | 2% |
| Carnuba Wax | 5% |
| Ascorbyl Palmitate | 1% |
| Tocopherol | 1% |

Example 5

A composition is prepared with the constituents specified in Table 5:

TABLE 5

| Formulation E | |
|---|---|
| Ingredient | Weight % of Composition |
| Cupuaçu butter | 32% |
| *Murmuru* butter | 16% |
| Castor seed oil | 5% |
| *Rhus Vernicflua* Peel Cera | 1% |
| *Rhus Succedanea* Fruit Cera | 1% |
| Ascorbyl Palmitate | 1% |
| Tocopherol | 1% |

Example 6

A composition is prepared with the constituents listed in Tables 1-5, wherein the composition exhibits improved stability compared to traditional lip balms, which can become extremely soft and melt in hot environments, such as in a car, a purse, or a pocket.

The composition, suitably when prepared in a stick formulation, shows greater stick stability with improved needle penetration values. These improved results indicate that the composition is more rigid, or hard, and is able to maintain form, shape, and/or structure, even in environments with elevated temperatures. The improved stick formulation can still be applied easily and smoothly to the surface of the lips or skin.

What is claimed is:

1. A lip and skin tissue balm composition comprising:
   (a) a first low-melt wax;
   (b) a second low-melt wax that is different from the first low-melt was of (a);
   (c) a high-melt wax;
   (d) one or more oil phases; and
   (e) optionally a flavoring agent;
   wherein the high melt wax has a melting temperature of greater than about 50° C. and is present in an amount of about 18.6% to about 27.0% by weight,
   wherein the ratio of the first and second low-melt waxes to the high-melt wax is about 1:1 to about 2:1, and
   wherein the composition is a solid until the composition is contacted with a tissue and energy is applied to transform the contacted composition into a melt form.

2. The composition of claim 1, wherein the first low-melt wax comprises Cupuaçu (*Theobroma grandiforum*) butter.

3. The composition of claim 2, wherein the Cupuaçu butter is present in an amount of about 15% to about 45% by weight.

4. The composition of claim 2, wherein the Cupuaçu butter is present in an amount of about 28% to about 38% by weight.

5. The composition of claim 1, wherein the second low-melt wax comprises *Murumuru* (*Astrocaryum murumuru*) butter.

6. The composition of claim 5, wherein the *Murumuru* butter is present in an amount of about 15% to about 45% by weight.

7. The composition of claim 5, wherein the *Murumuru* butter is present in an amount of about 25% to about 35% by weight.

8. The composition of claim 1, wherein the high-melt wax comprises beeswax.

9. The composition of claim 1, wherein the high-melt wax comprises carnauba wax.

10. The composition of claim 1, wherein the one or more oil phases is present in an amount from about 1.0% to about 7.7% by weight.

11. The composition of claim 10, wherein the one or more oil phases comprises sunflower oil.

12. The composition of claim 11, wherein the sunflower oil is present in an amount of about 5.0% by weight.

13. The composition of claim 10, wherein the one or more oil phases comprises cranberry seed oil.

14. The composition of claim 10, wherein the one or more oil phases comprises daikon seed oil.

15. The composition of claim 10, wherein the one or more oil phases comprises olive oil.

16. The composition of claim 10, wherein the one or more oil phases comprises cranberry seed oil and daikon seed oil.

17. The composition of claim 16, wherein the cranberry seed oil is present in an amount of about 1.0% by weight and the daikon seed oil is present in an amount of about 6.7% by weight.

18. The composition of claim 1, wherein the flavor is present in an amount of about 6%.

19. The composition of claim 1, wherein the combined total weight of the first low-melt wax and the second low-melt wax is present in an amount from about 30% to about 80% by weight.

20. The composition of claim 1, wherein the combined total weight of the first low-melt wax and the second low-melt wax is present in an amount from about 50% to about 70% by weight.

21. The composition of claim 1, wherein the ratio of the first low-melt wax to the second low-melt wax is about 1:1.

22. The composition of claim 1, wherein the ratio of the first and second low-melt waxes to the one or more oil phases is about 2.5:1 to about 11:1.

23. The composition of claim 1, wherein the melting temperature is between about 25° C. and about 37° C.

24. The composition of claim 1, wherein the energy is pressure or shearing.

* * * * *